(12) United States Patent
Matsushige et al.

(10) Patent No.: US 8,883,875 B2
(45) Date of Patent: Nov. 11, 2014

(54) KIT FOR ADHESION BETWEEN ALGINATE IMPRESSION MATERIAL FOR DENTAL USE AND IMPRESSION TRAY

(75) Inventors: Kouji Matsushige, Tokyo (JP); Makoto Oguri, Tokyo (JP)

(73) Assignee: Tokuyama Dental Corporation, Tokyo (JP)

( * ) Notice: Subject to any disclaimer, the term of this patent is extended or adjusted under 35 U.S.C. 154(b) by 73 days.

(21) Appl. No.: 13/696,669

(22) PCT Filed: May 10, 2011

(86) PCT No.: PCT/JP2011/060713
§ 371 (c)(1),
(2), (4) Date: Nov. 7, 2012

(87) PCT Pub. No.: WO2011/142335
PCT Pub. Date: Nov. 17, 2011

(65) Prior Publication Data
US 2013/0068132 A1    Mar. 21, 2013

(30) Foreign Application Priority Data

May 11, 2010    (JP) ................................. 2010-108929

(51) Int. Cl.
| | | |
|---|---|---|
| *A61K 6/10* | (2006.01) | |
| *A61C 9/00* | (2006.01) | |
| *A61K 6/083* | (2006.01) | |
| *C09J 139/02* | (2006.01) | |

(52) U.S. Cl.
CPC ............. *C09J 139/02* (2013.01); *A61C 9/0006* (2013.01); *A61K 6/10* (2013.01); *A61K 6/083* (2013.01)
USPC .............. 523/109; 523/118; 106/35; 433/214

(58) Field of Classification Search
USPC ..................... 523/109, 118; 106/35; 433/214
See application file for complete search history.

(56) References Cited

U.S. PATENT DOCUMENTS

| | | | | |
|---|---|---|---|---|
| 5,203,914 | A * | 4/1993 | Futami et al. ................... | 106/35 |
| 6,852,774 | B1 | 2/2005 | Engelbrecht | |
| 8,686,065 | B2 * | 4/2014 | Oguri et al. ................... | 523/118 |
| 2007/0232717 | A1 * | 10/2007 | Kamohara et al. ............. | 523/109 |
| 2010/0120941 | A1 | 5/2010 | Oguri et al. | |

FOREIGN PATENT DOCUMENTS

| | | |
|---|---|---|
| JP | 10-175812 A | 6/1998 |
| JP | 2000-160106 A | 6/2000 |
| JP | 2001-017449 A | 1/2001 |
| JP | 2001-329229 A | 11/2001 |
| JP | 2002-541164 A | 12/2002 |
| JP | 2007-262010 A | 10/2007 |
| JP | 2009-023958 A | 2/2009 |
| JP | 2009-046424 A | 3/2009 |
| JP | 2010-057905 A | 3/2010 |
| WO | 2008-105452 A1 | 9/2008 |

OTHER PUBLICATIONS

International Search Report Dated May 26, 2011, Mailed Jun. 7, 2011.
Translation of Search Report Dated May 26, 2011, Mailed Jun. 7, 2011.

* cited by examiner

*Primary Examiner* — Tae H Yoon
(74) *Attorney, Agent, or Firm* — Norris McLaughlin & Marcus PA

(57) ABSTRACT

Disclosed is a kit for adhesion between an alginate impression material for dental use and an impression tray, which contains: (U) a pretreatment agent that contains (I) 100 parts by mass of an organic solvent that has a solubility parameter (δ) of 17.0-23.0 $[(MPa)^{1/2}]$ and (II) 0.1-30 parts by mass of inorganic particles having an average particle diameter of 10 μm or less; and (V1) an adhesive that contains (I) a polyamine compound that contains two or more amino groups in each molecule and (III) a lower alcohol solvent, or (V2) an adhesive that is obtained by mixing (I) a polyamine compound that contains two or more amino groups in each molecule, (II) an organic peroxide and (III) a lower alcohol solvent.

9 Claims, No Drawings

KIT FOR ADHESION BETWEEN ALGINATE IMPRESSION MATERIAL FOR DENTAL USE AND IMPRESSION TRAY

This application is a 371 application of PCT/JP2011/060173 filed May 10, 2011, which claims foreign priority benefit under 35 U.S.C. §119 of Japanese application 2010-108929 filed Nov. 5, 2010.

TECHNICAL FIELD

The present invention relates to a kit for adhesion used to bond an alginate impression material and an impression tray at the time of dental treatment or the like. More particularly, the present invention relates to the kit for adhesion composed of a pretreatment agent and an adhesive.

BACKGROUND ART

When teeth have defects and the like, it is necessary to restore such defects. When defects and the like are to be restored, there are occasions where a cast crown restoration treatment, a defect prosthetic treatment or the like is needed. In this case, first, a mold having a negative form that replicates the shape of an abutment tooth, which has been subjected to a basic treatment or the like, is taken. Subsequently, by using the mold thus obtained, a cast of the abutment tooth or the like is produced using plaster or the like. Thereafter, a prosthesis is produced by utilizing the cast thus produced. Lastly, the prosthesis thus produced is installed on the abutment tooth or the like, and thereby the tooth is restored. This shape of an abutment tooth or the like is referred to as impression, and the curable material used to produce a solid mold that represents a specific shape by taking an impression is referred to as an impression material.

Generally, an alginate impression material, an agar impression material, a silicone rubber impression material, a polysulfide rubber impression material, a polyether rubber impression material, or the like is used as the impression material. Among these, an alginate impression material is most widely used because the material is inexpensive and easily handleable.

An alginate impression material includes a base material containing an alginic acid salt as a main component, and a curable material containing calcium sulfate as a main component. When the base material and the curable material are kneaded in the presence of water, a gel-like curable material is obtained. The alginate impression material is an impression material which utilizes the curing phenomenon described above.

The operation of taking an impression by using an alginate impression material (hereinafter, may be briefly described simply as "impression material") is carried out by the following procedure. First, a base material and a curable material are kneaded, and thus an impression material prior to curing is obtained. Subsequently, this impression material prior to curing is loaded on an impression tray which has replicated the dentition. Thereafter, the tray loaded with the impression material is pressed against the teeth such that the teeth in the oral cavity are wrapped up by the impression material. Lastly, after the impression material cures, the impression material that has adhered to the tray and is integrated therewith is removed from the teeth, and the impression material is withdrawn from the oral cavity together with the tray.

The tray used to take an impression is roughly classified into two types: stock trays and custom trays. The stock trays are trays having ready-made sizes and shapes. Specific examples of the stock trays include trays made of metals such as stainless steel, brass, and brass provided with chrome plating. The custom trays are trays that are produced with separate shapes in accordance with different individuals. Specific examples of the custom tray include resin trays formed from polymethacrylic acid esters, and trays made of modeling compounds formed from thermoplastic resins. Meanwhile, as the polymethacrylic acid esters that serve as the material of resin trays, usually polymethyl methacrylate, polyethyl methacrylate, a methyl methacrylate-ethyl methacrylate copolymer, and the like are used.

Since alginate impression materials have low adhesiveness to the various trays described above, when an impression material is removed from the teeth, there are occasions in which the impression material is detached from the tray. When the impression material is detached from the tray, the shape of the impression taken is likely to change significantly. Therefore, when the impression material is detached, there is a problem that a highly accurate impression cannot be taken.

In order to address the problem described above, a method of using a reticulated tray, an undercut-shaped tray or a tray having punched holes, may be contemplated. When a tray having such a shape is used, the contact area between the tray and the impression material increases, and the holding power between the impression material and the tray is enhanced. As a result, the impression material is not easily detached from the tray.

On the other hand, in the case of using, not a tray having a shape such as described above, but a stock tray or custom tray which is plate-shaped with a smooth surface, it is necessary to increase the holding power between the impression material and the tray by any means.

Regarding a method of increasing the holding power, there is a method of increasing the holding power between a tray and an impression material by applying, between the two members, an adhesive containing a fine powder and an organic solvent (see Patent Document 1). As the solvent, resin-swellable organic solvents (for example, xylene, toluene and ethyl acetate) are used. The solubility parameters ($\delta$) of these solvents are in the range of 17.0 to 20.5 $[(MPa)^{1/2}]$.

As another method, a method of bonding a tray and an impression material by using an adhesive containing a polyamine compound containing two or more amino groups in one molecule, a solvent, and suitably an organic peroxide (see Patent Document 2) is available.

In the adhesive disclosed in Patent Document 1, a resin-swellable organic solvent having a solubility parameter value which is within the range of solubility parameter described above, is used as the solvent. The action of this organic solvent is to swell and dissolve the surface of the tray, and to attach the fine powder component to the tray surface. The adhesive force between the tray and the impression material is a force that is increased only by the physical interlocking force between the fine powder component and the impression material. Therefore, in the case where the system depends on the increase of the adhesive force based on physical interlocking force as such, fluctuations in the adhesive force cannot be prevented from occurring. Furthermore, this adhesive is effective for a tray made of a resin or a tray made of a modeling compound, which are both swellable in the presence of an organic solvent. However, when the adhesive is used for a tray made of a metal, the adhesive force increasing effect is hardly recognized.

On the other hand, in the adhesive disclosed in Patent Document 2, crosslinking is formed between the amino groups carried by the polyamine compound and the carboxyl groups carried by the alginate impression material that are incorporated.

Furthermore, since the polyamine compound has high affinity with various tray materials, high adhesive force is exhibited not only with a tray made of a resin or a tray made of a modeling compound, but also with a tray made of a metal. As a result, the adhesive force between the various trays described above and impression materials is fairly high.

However, the adhesive force between a tray and an impression material exhibited by the aforementioned adhesive is still not satisfactory for the purpose of practical use, and there is room for further improvement.

Particularly, in the case of bonding an impression material to a resin tray by using this adhesive, and taking an impression in the oral cavity, it was found that if the contact pressure to press the impression material loaded on the tray against the teeth is insufficient, the adhesive force between the tray and the impression material decreases. Specifically, an area where a relatively high contact pressure (100 gf/cm$^2$ or greater) is exerted, such as a site where the teeth collide with the tray, is satisfactorily bonded. However, at an area where a relatively weak contact pressure (20 gf/cm$^2$ or less) is exerted, such as the rim of the tray, the adhesive force decreases.

On the other hand, in order to increase the adhesive force between the tray and the impression material, a method of increasing the surface roughness of the tray made of a resin is available. As a method of increasing the surface roughness, a method of subjecting the tray surface to a polishing treatment (grinding the surface using a dental turbine or the like) or to a sand blast treatment, may be used. In the case of a tray with high surface roughness (usually, in terms of the value (Ra) measured with a contact type surface roughness meter according to JIS B 0601, a tray having a surface roughness of greater than 1.0 μm), an alginate impression material can be bonded to the tray with high adhesive force by using the adhesive described above. However, in the case of a resin tray which has not been subjected to such a treatment (having a surface that has not be roughened) (the surface roughness (Ra) is 1.0 μm or less), the tray and the impression material cannot be bonded with sufficient strength even if the aforementioned adhesive is used.

Under such circumstances, the inventors of the present invention conducted an investigation to use, in this adhesive of Patent Document 2, a resin-swellable organic solvent having a solubility parameter value in the range described above in particular as a solvent, and further to incorporate inorganic particles having an average particle size of 10 μm or less. As a result, the inventors found that this adhesive exhibits a markedly increased adhesive force against a tray made of a resin, and previously proposed the adhesive (see Patent Document 3). That is, in the case of using a tray made of a resin, even if the contact pressure against the teeth and the like is week, or even if a tray having a smooth surface that has not been polished is used, the tray and the impression material are strongly bonded using the improved adhesive as described above.

Patent Document 1: Japanese Patent No. 3778731
Patent Document 2: International Application WO 2008/105452
Patent Document 3: Japanese Patent Application Laid-Open No. 2010-57905

SUMMARY OF INVENTION

Technical Problem

With regard to the adhesive of Patent Document 3, the inventors of the present invention conducted investigations more extensively. As a result, it was found that most of the organic solvents, which are listed as examples of the organic solvent which is resin-swellable and has a solubility parameter value in the range described above, cannot be used for the following reason. It is because when these organic solvents are caused to co-exist with a polyamine compound in a one-liquid state, the system turns into gel under storage for merely several days, and cannot be used as an adhesive. Furthermore, considering this gelation, it is speculated that even in the times before gelation of this adhesive is recognized, interaction of various components that brings about gelation has been in progress in the adhesive. That is, there is a concern that since the beginning of the time when a one-liquid adhesive is prepared, some kind of interaction between various components, which has adverse influence on the adhesiveness, has already been underway.

Under such circumstances, an object of the present invention is to develop an adhesive for bonding an impression material and a tray, which exhibits high adhesive force against any of trays made of metals and trays made of resins, and is capable of long-term storage, that is, capable of maintaining the adhesive effect for a long time period.

Solution to Problem

In order to achieve the object described above, the inventors of the present invention conducted a thorough investigation. As a result, the inventors of the present invention conceived that an adhesive obtained by incorporating a polyamine compound, a lower alcohol-based solvent and optionally an organic peroxide, is combined with an adhesive containing an organic solvent having a solubility parameter value in the range of resin-swellable solubility parameters described above, and inorganic particles, as a pretreatment agent. The inventors of the present invention found, through the contemplation as described above, that the problems described above were solved, and thus finally completed the present invention.

According to an aspect of the present invention, a kit for adhesion between an alginate impression material for dental use and an impression tray comprising:

(U) a pretreatment agent containing 100 parts by mass of (I) an organic solvent having a solubility parameter (δ) of 17.0 to 23.0 [(MPa)$^{1/2}$], and 0.1 parts to 30 parts by mass of (II) inorganic particles having an average particle size of 10 μm or less; and (V) an adhesive containing (I) a polyamine compound containing two or more amino groups in one molecule, and (III) a lower alcohol-based solvent. According to another aspect of the present invention, a kit for adhesion between an alginate impression material for dental use and an impression tray comprising:

(U) a pretreatment agent containing 100 parts by mass of (I) an organic solvent having a solubility parameter (δ) of 17.0 to 23.0 [(MPa)$^{1/2}$], and 0.1 parts to 30 parts by mass of (II) inorganic particles having an average particle size of 10 μm or less; and (V) an adhesive obtained by mixing (I) a polyamine compound containing two or more amino groups in one molecule, (II) an organic peroxide, and (III) a lower alcohol-based solvent.

Advantageous Effects of Invention

The kit for adhesion of the present invention is composed of a pretreatment agent and an adhesive. The (V) adhesive of the adhesive kit of the present invention is such that, even though the adhesive contains (I) a polyamine compound, the adhesive does not undergo gelation even after long-term storage, and has excellent storage stability. This effect is attributable to the fact that the (III) solvent contained in the (V) adhesive is a lower alcohol-based solvent, and has a solubility parameter value which is not in the range of solubility parameter values that cause resin-swellability.

The adhesive kit of the present invention can stably bond an alginate impression material and impression trays of various materials, with high adhesive force. Furthermore, surprisingly, the intensity of the adhesive force is superior to that of the adhesive disclosed in Patent Document 3, which contains a polyamine compound, a solvent and an organic peroxide, wherein an organic solvent having a solubility parameter value in the range of resin-swellable solubility parameters is used as the solvent, and inorganic particles are also incorporated.

Particularly, in connection with a tray made of a resin, when the contact pressure of the impression material against to the tray is as weak as 20 gf/cm$^2$ or less, or when the surface roughness of the tray made of a resin is small (Ra=1.0 μm or less, and more preferably 0.05 μm to 0.2 μm), the adhesive force is maintained high.

The cause by which high adhesive force is obtained is not clearly known. However, it is contemplated that when the resin-swellable organic solvent and a polyamine compound are caused to co-exist in a one-liquid state, interaction of these various components is underway from the initial stage prior to gelation, and this interaction exerts some kind of adverse influence on the adhesive force between a tray made of a resin or the like and an impression material. On the other hand, in the present invention, it is speculated that since the (U) pretreatment agent and the (V) adhesive are separated apart, this adverse influence does not take effect.

DESCRIPTION OF EMBODIMENTS

Hereinafter, suitable embodiments of the adhesive kit for adhering between an alginate impression material for dental use and an impression tray according to the present invention will be described. However, the present invention is not intended to be limited to the embodiments that will be described below.

[Pretreatment Agent]

First, the (U) pretreatment agent containing 100 parts by mass of (I) an organic solvent having a solubility parameter (δ) value of 17.0 to 23.0 [(MPa)$^{1/2}$], and 0.1 parts to 30 parts by mass of (II) inorganic particles having an average particle size of 10 μm or less, will be explained. Since this pretreatment agent is capable of strongly bonding primarily a tray made of a resin and an alginate impression material, the pretreatment agent is useful for the use in pretreatment.

The organic solvent needs to have sufficient dissolving power against resins such as polymethyl methacrylate, which is representative as a material for trays made of resins. An organic solvent having a solubility parameter (δ) value of 17.0 to 23.0 [(MPa)$^{1/2}$] has a noticeable action of swelling and dissolving the surface of a tray made of a resin, and fixing inorganic particles to the surface of the tray made of resin. For the above reason, an organic solvent having a solubility parameter (δ) value in the above-described range of 17.0 to 23.0 [(MPa)$^{1/2}$] is used as the organic solvent to be incorporated into the pretreatment agent of the present invention.

Specific preferred examples of the organic solvent include butyl acetate (17.4), dimethyl ether (18.0), xylene (18.1), toluene (18.2), tetrahydrofuran (18.6), ethyl acetate (18.6), benzene (18.8), dibutyl phthalate (19.0), methyl ethyl ketone (19.0), chloroform (19.0), methylene chloride (19.8), acetone (20.3), o-dichlorobenzene (20.5) and the like. The numbers in the parentheses represent the solubility parameter values.

If the solubility parameter (δ) of the organic solvent is smaller than 17.0 [(MPa)$^{1/2}$] or greater than 23.0, this organic solvent cannot sufficiently swell and dissolve the tray made of a resin. From the viewpoint of the extent of the good solubility to dissolve the tray made of a resin, an organic solvent having a solubility parameter (δ) value in the range of 18.0 to 22.0 [(MPa)$^{1/2}$] is preferred. When an emphasis is added to the viewpoint of biological safety, xylene, toluene and ethyl acetate are most preferred. These organic solvents can be used as mixtures.

In order to enhance the dispersibility of inorganic particles and the handleability of the pretreatment agent, other organic solvents can be added in addition to those described above. Specific examples of such solvents include alcohols such as methanol, ethanol, isopropyl alcohol, and butanol. In the case of including these other organic solvents, the solubility parameter value of the solvent mixture should be adjusted to the range described above in order to maintain swellability or solubility against the tray made of a resin.

The inorganic particles having an average particle size of 10 μm or less that are incorporated into the pretreatment agent of the present invention, impart an action of increasing the adhesive force against an impression material, to a tray made of a resin or a tray made of a modeling compound, particularly to a tray made of a resin. That is, through the action of the organic solvent described above, the surface of a tray made of a resin is sufficiently swollen and dissolved, and thus has been roughened. The action of the inorganic particles is such that the inorganic particles are fixed to this tray surface that has been roughened, and further roughen the surface of the tray made of a resin that has been sufficiently roughened. At the time of taking an impression, the impression material is pressed against this roughened tray made of a resin. As a result, the impression material penetrates by replicating the surface unevenness of the tray, and the physical interlocking force, produced between the two members as a result, causes a large increase in the adhesive force between the tray surface and the impression material surface.

There are no particular limitations on the inorganic particles, and specifically, silica glass, borosilicate glass, soda glass, aluminosilicate glass, and fluoroaluminosilicate glass, and glass containing heavy metals (for example, barium, strontium, and zirconium); glass ceramics such as crystallized glass having crystals precipitated in those glass materials, and crystallized glass having crystals of diopside, leucite and the like precipitated therein; and complex inorganic oxides such as silica-zirconia, silica-titania, and silica-alumina, can be used.

Alternatively, oxides obtained by adding oxides of Group I metals to these composite oxides; metal inorganic oxides such as silica, alumina, titania and zirconia; and the like can be used.

Among these, silica glass, fluoroaluminosilicate glass, and metal oxides such as silica, silica-titania, and silica-zirconia are suitable. These can be used singly, or admixtures of two or more kinds.

In order to enhance the dispersibility of the inorganic particles in the organic solvent, it is preferable to carry out a surface treatment of the inorganic particles by using a silane coupling agent or the like. Regarding the silane coupling agent, any known silane coupling agent can be used. The surface treatment method is also not particularly limited, and any known method can be employed. A specific example may be a method of dispersing and mixing inorganic particles and a coupling agent in an appropriate solvent by using a ball mill or the like, subsequently drying the mixture by using an evaporator or a spray dryer, and then heating the dried mixture at 50° C. to 150° C. Another example may be a method of heating inorganic particles and a coupling agent in a solvent such as an alcohol under stirring.

In regard to the particle size of the inorganic particles used in the pretreatment agent, from the viewpoint of increasing the physical interlocking force between the tray made of a resin and the impression material and thereby exhibiting high adhesive force, the average particle size needs to be 10 μm or less. Furthermore, considering that it is necessary for the inorganic particles to be not likely to submerge in a solvent, the average particle size of the inorganic particles is preferably 3 μm or less, and particularly suitably 1 μm or less. If the average particle size of the inorganic particles is extremely small, the viscosity of the adhesive increases too high. Therefore, the average particle size is preferably 0.001 μm or greater, and more preferably 0.010 μm or greater. According to the present invention, the average particle size of the inorganic particles refers to the value measured by using a particle size distribution analyzer which uses a light diffraction method.

There are no particular limitations on the shape of the inorganic particles. Particles having any shape, such as spherical or approximately spherical particles that are synthesized according to a sol-gel method, and irregularly shaped particles obtainable by pulverization, can be used.

The amount of incorporation of the inorganic particles in the pretreatment agent is 0.1 parts to 30 parts by mass relative to 100 parts by mass of the organic solvent. In the case of this amount of incorporation, satisfactory adhesiveness is obtained. When the viscosity of the liquid and the coatability on the tray are considered, the amount of incorporation is preferably 1 part to 10 parts by mass relative to 100 parts by mass of the organic solvent.

For the pretreatment agent, an organic thickening material containing a polymer compound such as polyvinylpyrrolidone, carboxymethyl cellulose or polyvinyl alcohol; or various additives such as an ultraviolet absorber, a dye, an antistatic agent, a pigment and a fragrance may be appropriately incorporated to the extent that the adhesive force between the impression material and the tray is not decreased.

The pretreatment agent can be prepared by mixing and dispersing inorganic particles having the average particle size described above in an organic solvent having the solubility parameter value described above. The method of mixing is not particularly limited. Examples of the mixing method include conventional mixing by means of a magnetic stirrer, a stirring blade or the like; ultrasonic dispersion, dispersion by a Disperser, and dispersion by a wet ball mill.

[Adhesive]

The adhesive will be explained below.

Adhesive of First Embodiment

First, the adhesive of the first embodiment will be explained. This (V1) adhesive contains (I) a polyamine compound containing two or more amino groups in one molecule and (III) a lower alcohol-based solvent.

The (V1) adhesive contains (I) a polyamine compound having two or more amino groups ($-NH_2$) in one molecule. Therefore, when an impression material is loaded on a tray which has been treated with a pretreatment agent, crosslinking is formed between the amino group of the polyamine compound and the carboxyl group of the alginate impression material. As a result, it is speculated that the adhesiveness between the alginate impression material and the tray increases. Furthermore, since polyamine compounds have high affinity particularly with trays made of metals, a polyamine compound strongly adheres thereto when brought into contact with a tray made of a metal.

Examples of the polyamine compound that may be used in the adhesive include ethylenediamine, 1,4-butanediamine, 1,7-heptanediamine, 4-(aminomethyl)-1,8-octanediamine, tris(2-aminoethyl)amine, and aliphatic polyamine compounds having two or more amino groups in one molecule, such as triethylenetetraamine, pentaethylenehexaamine, and trip ropylenetetraamine.

Further examples include alicyclic polyamine compounds having two or more amino groups in one molecule, such as 1,2-diaminocylohexane, 1,4-diaminocyclohexane, and 1,3-cyclohexanebis(methylamine).

Furthermore, other examples include aromatic compounds having two or more amino groups in one molecule, such as 1,3-phenylenediamine, 3,3'-methylenedianiline, 1,2,4-triaminobenzene, diaminoalkanes, 1,3,5-triazine-2,4,6-triamine, and 3,3'-diaminobenzidine.

Still further examples include polymers or copolymers obtained by polymerizing monomers having one or more amino groups, such as polyallylamine, polyvinylamine, polyethyleneimine, polyornithine, polylysine, and chitosan. These can be used singly or as mixtures of two or more kinds.

Among the polyamine compounds, from the viewpoint of obtaining stable adhesive force, a polyamine compound having 5 or more, and more preferably 15 or more, amino groups in one molecule, such as polyallylamine, polyvinylamine, polyethyleneimine, polyornithine, polylysine, or chitosan, is preferred.

The molecular weight of the polyamine compound is not particularly limited. When solubility in a lower alcohol as a solvent is considered, the molecular weight of the polyamine compound is preferably 500,000 or less, and more preferably 1,000 to 20,000. In the case of a polyamine compound having a molecular weight of 2,000 or greater, in order to obtain sufficiently high adhesive force, a polyamine compound containing one or more amino groups per a molecular weight of 300 is preferred, and a polyamine compound containing one or more amino groups per a molecular weight of 200 is more preferred.

The amount of incorporation of the polyamine compound is preferably 1 part to 50 parts by mass, more preferably 2 parts to 45 parts by mass, and most preferably 15 parts to 30 parts by mass, relative to 100 parts by mass of the adhesive.

The (V1) adhesive of the first embodiment contains (III) a lower alcohol-based solvent.

The (III) lower alcohol-based solvent is incorporated into the adhesive as a diluent solvent for the polyamine compound. The lower alcohol-based solvent is incorporated to enhance the handleability of the adhesive (coatability on the tray). As discussed above, when an organic solvent having a solubility parameter ($\delta$) value in the range of 17.0 to 23.0 $[(MPa)^{1/2}]$ is incorporated into the adhesive, the adhesive usually turns into gel within several days.

On the other hand, when a lower alcohol-based solvent is incorporated into the adhesive, gelation of the adhesive over a long time period is suppressed even if the solvent co-exists with such a polyamine compound. Meanwhile, the solubility parameter ($\delta$) values of these lower alcohol-based solvents are usually in the range of 23.3 to 30.0 $[(MPa)^{1/2}]$, and the solubility parameter values are larger than the upper limit in the range for resin swellability, 23.0 $[(MPa)^{1/2}]$. However, with regard to this adhesive, since it is not necessary to impart an action of swelling and dissolving a tray made of a resin as in the case of the pretreatment, and this lower alcohol-based solvent can dissolve the polyamine compound satisfactorily, there is no problem even if the solubility parameter value of the lower alcohol-based solvent exceeds the range described above. Moreover, these lower alcohol-based solvents can be easily dried because of their high volatility, and are generally less toxic. Therefore, the lower alcohol-based solvents are preferred.

Here, it is contemplated that the reason why the adhesive does not turn into gel when a lower alcohol-based solvent is used is that the highly reactive amino groups of the polyamine are protected by the alcoholic hydroxyl groups.

Meanwhile, solvents generally include organic solvents having solubility parameter values that are smaller than the lower limit of the resin-swellable range, such as heptane, and organic solvents other than alcohol-based solvents, having solubility parameter values that are larger than the upper limit of the resin-swellable range (for example, acetonitrile). However, when these solvents are used instead of alcohol-based solvents, the effect of suppressing the gelation of the adhesive is usually insufficient.

A lower alcohol-based solvent according to the present invention means an aliphatic alcohol having 1 to 5 carbon atoms. Specific examples include methanol, ethanol, isopropyl alcohol, and n-butanol. From the viewpoint of biological safety, ethanol is particularly preferred.

The amount of incorporation of the alcohol-based solvent is, from the viewpoint of the handleability of the adhesive (coatability on the tray), preferably 20 parts to 98.9 parts by mass, more preferably 50 parts to 97 parts by mass, and most preferably 65 parts to 73 parts by mass, relative to 100 parts by mass of the adhesive.

The adhesive may also appropriately contain, as other components, various additives such as an ultraviolet absorber, a dye, an antistatic agent, a pigment and a fragrance, to the extent that the adhesive force between the impression material and the tray is not decreased.

The adhesive containing the aforementioned various components can be prepared by mixing a polyamine compound and a lower alcohol-based solvent, and dissolving the polyamine compound. There are no particular limitations on the mixing method. In addition to conventional mixing methods using a magnetic stirrer or a stirring blade, an ultrasonic dispersion method and the like may also be used.

Adhesive of Second Embodiment

In the adhesive (V2) of the second embodiment, an organic peroxide is further incorporated in addition to the constituent components of the adhesive (V1) of the first embodiment. That is, the (V2) adhesive of the second embodiment is an adhesive obtained by mixing (I) a polyamine compound containing two or more amino groups in one molecule, (II) an organic peroxide, and (III) a lower alcohol-based solvent.

The incorporation of an organic peroxide is important particularly for enhancing the adhesive force of the impression material to a tray made of a resin. The adhesive of the second embodiment is usually commercially available and is supplied for use as a kit together with the pretreatment agent, as in the case of the adhesive of the first embodiment.

Examples of the organic peroxide include diacyl peroxides, peroxyesters, dialkyl peroxides, peroxydicarbonates, peroxyketals, ketone peroxides, and hydroperoxides.

Among these, when diacyl peroxides are used, the tray made of a resin and the impression material adhere to each other more strongly. Specific examples of the diacyl peroxides include benzoyl peroxide, stearoyl peroxide, 2,4-dichlorobenzoyl peroxide, and m-toluoyl peroxides.

Regarding the amount of incorporation of the organic peroxide, in order to obtain sufficiently strong adhesive force, it is preferable to incorporate the organic peroxide in an amount of 0.1 parts to 30 parts by mass, and more preferably 1 part to 12 parts by mass, relative to 100 parts by mass of the adhesive.

In the adhesive, various additives such as an ultraviolet absorber, a dye, an antistatic agent, a pigment and a fragrance may be appropriately incorporated to the extent that the adhesive force between the impression material and the tray is not decreased.

The (V2) adhesive of the second embodiment containing the aforementioned various components can be prepared by mixing a polyamine compound and an organic peroxide with a lower alcohol-based solvent, and dissolving the components. There are no particular limitations on the mixing method, but conventional mixing methods using a magnetic stirrer or a stirring blade can be employed. Mixing may also be carried out by an ultrasonic dispersion method.

In regard to the kit for adhesion according to the embodiment of the present invention, the (U) pretreatment agent containing 100 parts by mass of (I) an organic solvent having a solubility parameter (δ) of 17.0 to 23.0 $[(MPa)^{1/2}]$, and 0.1 parts to 30 parts by mass of (II) inorganic particles having an average particle size of 10 μm or less, needs to be used as a pretreatment agent.

That is, it is not allowed to apply (V1) an adhesive containing (I) a polyamine compound containing two or more amino groups in one molecule, and (III) a lower alcohol-based solvent, or (V2) an adhesive obtained by mixing (I) a polyamine compound containing two or more amino groups in one molecule, (II) an organic peroxide, and (III) a lower alcohol-based solvent, as a pretreatment agent on a tray, and subsequently apply the (U) pretreatment.

In the case of conducting the application by the procedure described above, the surface on which the adhesive of (V1) or (V2) is applied is disarranged by the operation of applying the (U) pretreatment agent that is carried out thereafter. As a result, when the impression material is loaded on the tray, the crosslinking reaction between the polyamine compound contained in the adhesive of (V1) or (V2) and the carboxyl groups in the impression material does not proceed satisfactorily, and the adhesive force between the two members is decreased to a large extent.

The method for applying the pretreatment agent and the adhesive on the tray is not particularly limited. In general, methods of applying the pretreatment agent or the adhesive on the tray with a brush, a spatula, a paintbrush, a roller or the like, or spraying the pretreatment agent and the adhesive on the tray can be employed.

After the pretreatment agent or the adhesive is applied or sprayed on the tray, preferably, the agent is dried, and the solvent is evaporated. Examples of the drying method include natural drying, drying under heating, drying by air blowing, drying under reduced pressure, and hot air drying which combines drying under heating and drying by air blowing.

By using the kit for adhesion of the present invention, an alginate impression material and an impression tray of various materials, namely, a tray made of a resin, a tray made of a modeling compound and a tray made of a metal, can be stably bonded with high adhesive force. The pretreatment agent of the kit for adhesion of the present invention exhibits a high adhesive force enhancing effect against a tray made of a resin and a tray made of a modeling compound, particularly a tray made of a resin. Therefore, prior to the application of the adhesive, it is requested to apply the pretreatment agent on the tray.

As a matter of fact, the adhesive force enhancing effect attained by applying the pretreatment agent is also recognized in the case of a tray made of a metal. However, in the case of a tray made of a metal, since sufficient adhesive force can be obtained only with the adhesive, the pretreatment agent does not contribute as much as in the case of a tray made of a resin, in terms of enhancing the adhesive force. Accordingly, in the case of a tray made of a metal, the use of the pretreatment agent may be omitted.

As the alginate impression material to which the adhesive kit of the present invention can be applied, any known impression material may be used without any limitations. Specific types of the alginate impression material include an impression material of the type which uses a mixture with a base material paste containing an alginic acid salt as a main component and a curable material paste containing calcium sulfate as a main component; and an impression material of the type which uses by adding water to a mixture of a powder containing an alginic acid salt and calcium sulfate as main components.

To mention more specific, the base material paste of the alginate impression material of the type which uses a mixture of pastes, is composed of potassium alginate, a silica powder, potassium hydroxide, polyacrylic acid, water and the like. The curable material paste is composed of a granular silica, liquid paraffin, zinc oxide, magnesium oxide, trisodium phosphate, potassium fluorotitanate, ultrafine particulate silica, calcium sulfate, and the like.

In the alginate impression material of the type which uses by adding water to a powder and water, the powder is composed of potassium alginate, a silica powder, zinc oxide, magnesium oxide, trisodium phosphate, potassium fluorotitanate, calcium sulfate, and the like.

Hereinafter, the present invention will be specifically described by way of Examples, but the present invention is not intended to be limited to these Examples. Meanwhile, the adhesion test method is disclosed in section (1); the type of the tray used is disclosed in section (2); the evaluation methods are disclosed in section (3); and the compounds used in Examples and Comparative Examples are disclosed in section (4).

(1) Adhesion Test Method

A (U) pretreatment agent that had been prepared in advance was applied on the surface (surface for adhering) of each of trays made of various materials indicated in section (2) (surface of deposition) by using a paintbrush, and any excess solvent was evaporated by air blowing. Subsequently, an adhesive of (V1) or (V2) that had been prepared in advance was applied on the same surface for adhering by using a paintbrush, and any residual solvent was evaporated by air blowing. Thereafter, a kneaded alginate impression material was loaded on the surface for adhering of the tray, and the alginate impression material was left to stand for 3 minutes at 37° C. under a load of 130 gf/cm². Thereafter, the cured impression material was torn off from the tray.

Subsequently, the torn-off surface of the tray from which the cured impression material had been torn off was observed with the naked eye. With regard to the interface between the impression material and the tray, the proportion of the area where cohesive failure had occurred in the impression material was visually observed, and the adhesion performance was evaluated according to the evaluation criteria indicated in section (3). The alginate impression material used in all the adhesion tests was "AP-1 Paste" (manufactured by Tokuyama Dental Corp.), a paste type prepared by kneading using an AP Mixer II (manufactured by Tokuyama Dental Corp.).

In an adhesion test after a long-term storage, the (U) pretreatment agents and the adhesives of (V1) and (Q2) thus prepared were placed in sealed containers and stored for one week at 25° C. Subsequently, the same adhesion test as described above was carried out by using these stored pretreatment agents and adhesives.

(2) Type of Tray

"Ostron II" (manufactured by GC Corp.) was cured into a plate shape, and this was used as a simulation tray made of a resin. A plate was produced by loading a mixture of the powder and liquid of Ostron II on a polypropylene (PP) film, and curing the mixture while another PP polypropylene film was pressed thereon. The surface roughness of the plate was Ra=0.1 μm (measured with a contact type surface roughness meter (Surfcom, manufactured by Tokyo Seimitsu Co., Ltd.)).

As a tray made of a metal, a tray made of brass provided with a nickel plating, "COE104" (manufactured by GC Corp.) was used.

As a tray made of a modeling compound, "Modeling Compound Neutral" (manufactured by GC Corp.) was used (in the tables, briefly indicated as tray made of MC).

(3) Evaluation Criteria

VS: When the impression material and the tray are torn off by hand, cohesive failure of the impression material occurs in 90% or more of the adhesion area of the impression material.

S: When the impression material and the tray are torn off by hand, cohesive failure of the impression material occurs in more than or equal to 50% and less than 90% of the adhesion area of the impression material, but the impression material is detached from the interface with the tray in some parts.

W: When the impression material and the tray are torn off by hand, cohesive failure occurs in less than 50% of the adhesion area of the impression material, but most of the impression material is detached off from the interface with the tray.

VW: When the impression material and the tray are torn off by hand, the impression material is easily detached from the interface with the tray over the entire area.

(4) Abbreviations of compounds used in Examples and Comparative Examples (4-1) Organic Solvents: ($\delta$) [(MPa)$^{1/2}$]

Butyl acetate: 17.4
Xylene: 18.1
Toluene: 18.2
Ethyl acetate: 18.6
Acetone: 20.3
Ethanol: 26.0
IPA (isopropyl alcohol): 24.3
n-BuOH (n-butanol): 23.3
Heptane: 15.1
Acetonitrile: 24.1

(4-2) Inorganic Particles

F1: Rheorosil QS102 (amorphous silica, manufactured by Tokuyama Corp.) average particle size: 0.012 μm F2: Rheorosil ZD30ST (surface-treated amorphous silica, manufactured by Tokuyama Corp.) average particle size: 0.015 μm F3: Spherical silica-zirconia particles synthesized by a sol-gel method, average particle size: 0.9 μm F4: Irregular-shaped silica-zirconia particles synthesized by a sol-gel method, average particle size: 5 μm F5: Irregular-shaped silica-zirconia particles synthesized by a sol-gel method, average particle size: 30 μm Meanwhile, the measurement of the average particle size of the above inorganic particles was carried out by a particle size distribution analysis according to a light diffraction method (Coulter, manufactured by Beckman Coulter, Inc.)

(4-3) Polyamine Compound

PA1: 1,7-Heptanediamine

PA2: Polyallylamine (number of amino groups in one molecule: 16, molecular weight: 1,000)

PA3: Polyallylamine (number of amino groups in one molecule: 53, molecular weight: 3,000)

PA4: Polyallylamine (number of amino groups in one molecule: 263, molecular weight: 15,000)

(4-4) Organic Peroxide

BPO: Benzoyl peroxide
SPO: Stearoyl peroxide
BBTC: 1,1-Bis(t-butylperoxy)-3,3,5-trimethylsiloxane Example 1

As indicated in Table 1, 100 g of xylene as an organic solvent and 5 g of F1 as inorganic particles were weighed in a capped test tube. The test tube was irradiated with ultrasonic waves to disperse the particles, and thereby, a pretreatment agent (a) was prepared. Furthermore, as indicated in Table 2, 20 g of PA3 as a polyamine compound, 5 g of BPO as an organic peroxide, and 75 g of ethanol as an alcohol-based solvent were weighed in a capped test tube. The contents were stirred until BPO was dissolved, and thus an adhesive (C) was prepared. An adhesion test between the impression material and various trays was carried out by using the pretreatment agent and the adhesive thus obtained. Furthermore, the pretreatment agent and the adhesive thus prepared were left to stand for one week at 25° C. Thereafter, the same adhesion test was carried out. The results are presented in Table 3.

In all of the Examples, high adhesive force between the impression material and the trays was obtained. Also, none of the adhesives gelled even after a long-term storage (25° C., for one week), and the adhesion performance did not deteriorate with any one of the trays.

Examples 2 to 30

Adhesion tests were carried out in the same manner as in Example 1, except that the pretreatment agent and adhesive having the compositions indicated in Table 1 and Table 2 were used. The results are presented in Table 3. Under all conditions, the impression material and the trays adhered to each other strongly. Furthermore, none of the adhesives gelled even after a long-term storage, and high adhesion performance was maintained.

TABLE 1

| | Pretreatment agent composition/parts by mass | | | | | | | | | |
|---|---|---|---|---|---|---|---|---|---|---|
| | Organic solvent | | | | | | Inorganic particles | | | |
| | Xylene | Toluene | Ethyl acetate | Butyl acetate | Acetone | Ethanol | F1 | F2 | F3 | F4 |
| a | 100 | | | | | | 5 | | | |
| b | | 100 | | | | | 5 | | | |
| c | | | 100 | | | | 5 | | | |
| d | | | | 100 | | | 5 | | | |
| e | | | | 20 | 80 | | 5 | | | |
| f | | | | 60 | | 40 | 5 | | | |
| g | | 100 | | | | | | 5 | | |
| h | | 100 | | | | | | | 5 | |
| i | | 100 | | | | | | | | 5 |
| j | | | | 100 | | | 3.5 | | | |
| k | | | | 100 | | | 0.2 | | | |
| l | | | | 100 | | | 28 | | | |

TABLE 2

| | Adhesive composition/parts by mass | | | | | | | | | |
|---|---|---|---|---|---|---|---|---|---|---|
| | Polyamine compound | | | | Organic peroxide | | | Alcohol-based solvent | | |
| | PA1 | PA2 | PA3 | PA4 | BPO | SPO | BBTC | Ethanol | IPA | n-BuOH |
| A | 20 | | | | 5 | | | 75 | | |
| B | | 20 | | | 5 | | | 75 | | |
| C | | | 20 | | 5 | | | 75 | | |
| D | | | | 20 | 5 | | | 75 | | |
| E | | | 20 | | | 5 | | 75 | | |
| F | | | 20 | | | | 5 | 75 | | |
| G | | | 20 | | 5 | | | | 75 | |
| H | | | 20 | | 5 | | | | | 75 |
| I | | | 15 | | 5 | | | 80 | | |
| J | | | 30 | | 5 | | | 65 | | |
| K | | | 2 | | 5 | | | 93 | | |
| L | | | 45 | | 5 | | | 50 | | |
| M | | | 20 | | 0.5 | | | 79.5 | | |
| N | | | 20 | | 25 | | | 55 | | |
| O | 20 | | | | | | | 80 | | |
| P | | | | 20 | | | | 80 | | |
| Q | | | 20 | | | | | 80 | | |

TABLE 2-continued

| | Adhesive composition/parts by mass | | | | | | | | | |
|---|---|---|---|---|---|---|---|---|---|---|
| | Polyamine compound | | | | Organic peroxide | | | Alcohol-based solvent | | |
| | PA1 | PA2 | PA3 | PA4 | BPO | SPO | BBTC | Ethanol | IPA | n-BuOH |
| R | | | 20 | | 1 | | | 79 | | |
| S | | | 20 | | 12 | | | 68 | | |

TABLE 3

| | Pretreatment agent | | Adhesive No. | Initial adhesiveness | | | Adhesiveness after 1 week at room temperature | | |
|---|---|---|---|---|---|---|---|---|---|
| | No. | Solubility parameter | | Tray made of resin | Tray made of MC | Tray made of metal | Tray made of resin | Tray made of MC | Tray made of metal |
| Example 1 | a | 18.1 | C | VS | VS | VS | VS | VS | VS |
| Example 2 | b | 18.2 | C | VS | VS | VS | VS | VS | VS |
| Example 3 | c | 18.6 | C | VS | VS | VS | VS | VS | VS |
| Example 4 | d | 17.4 | C | S | S | VS | S | S | VS |
| Example 5 | e | 22.5 | C | S | S | VS | S | S | VS |
| Example 6 | f | 19.3 | C | VS | VS | VS | VS | VS | VS |
| Example 7 | g | 18.2 | C | VS | VS | VS | VS | VS | VS |
| Example 8 | h | 18.2 | C | VS | VS | VS | VS | VS | VS |
| Example 9 | i | 18.2 | C | S | S | S | S | S | S |
| Example 10 | j | 18.6 | C | VS | VS | VS | VS | VS | VS |
| Example 11 | k | 18.6 | C | S | S | VS | S | S | VS |
| Example 12 | l | 18.6 | C | S | S | VS | S | S | VS |
| Example 13 | c | 18.6 | A | VS | VS | S | VS | VS | S |
| Example 14 | c | 18.6 | B | VS | VS | VS | VS | VS | VS |
| Example 15 | c | 18.6 | D | VS | VS | VS | VS | VS | VS |
| Example 16 | c | 18.6 | E | VS | VS | VS | VS | VS | VS |
| Example 17 | c | 18.6 | F | VS | VS | VS | VS | VS | VS |
| Example 18 | c | 18.6 | G | VS | VS | VS | VS | VS | VS |
| Example 19 | c | 18.6 | H | VS | VS | VS | VS | VS | VS |
| Example 20 | c | 18.6 | I | VS | VS | VS | VS | VS | VS |
| Example 21 | c | 18.6 | J | VS | VS | VS | VS | VS | VS |
| Example 22 | c | 18.6 | K | VS | VS | S | VS | VS | S |
| Example 23 | c | 18.6 | L | VS | VS | S | VS | VS | S |
| Example 24 | c | 18.6 | M | S | S | VS | S | S | VS |
| Example 25 | c | 18.6 | N | S | S | VS | S | S | VS |
| Example 26 | c | 18.6 | O | S | S | VS | S | S | VS |
| Example 27 | c | 18.6 | P | S | S | VS | S | S | VS |
| Example 28 | c | 18.6 | Q | S | S | VS | S | S | VS |
| Example 29 | c | 18.6 | R | VS | VS | VS | VS | VS | VS |
| Example 30 | c | 18.6 | S | VS | VS | VS | VS | VS | VS |

Comparative Example 1

As shown in Table 4, 15 g of PA4 as a polyamine compound, 0.5 g of F2 as inorganic particles, 80 g of xylene as an organic solvent, and 4.5 g of BPO as an organic peroxide were weighed in a capped test tube, and the contents were irradiated with ultrasonic waves to disperse the inorganic particles. Thus, a one-liquid adhesive (composition of Example 32 of Patent Document 3) was prepared. An adhesion test was carried out on various trays by using this adhesive. Furthermore, the adhesive thus prepared was left to stand for one week at 25° C., and then the same adhesion test was carried out. The results are presented in Table 5. The adhesive immediately after preparation exhibited satisfactory adhesiveness for the adhesion between all the trays and the impression material. However, after being stored for one week at 25° C., gelation of the adhesive was observed.

Comparative Examples 2 to 4

Adhesion tests were carried out in the same manner as in Comparative Example 1, except that the one-liquid adhesives of the compositions indicated in Table 4 were used. The one-liquid adhesives used in these Comparative Examples were adhesives obtained by incorporating equal amounts of the polyamine compound (PA3) and the organic peroxide (BPO) that were incorporated into the adhesive C used in Examples 1 to 3, to the pretreatment agents (a), (b) and (c) used in Examples 1 to 3, respectively. The results are presented in Table 5.

TABLE 4

| | Polyamine compound | | Inorganic particles | Organic solvent | | | | Organic peroxide |
|---|---|---|---|---|---|---|---|---|
| | PA3 | PA4 | F2 | Xylene | Toluene | Ethyl acetate | Ethanol | BPO |
| Comparative Example 1 | | 15 | 0.5 | 80 | | | | 4.5 |
| Comparative Example 2 | 20 | | 5 | 70 | | | | 5 |
| Comparative Example 3 | 20 | | 5 | | 70 | | | 5 |
| Comparative Example 4 | 20 | | 5 | | | 70 | | 5 |

TABLE 5

| | Solubility parameter δ | Initial adhesiveness | | | Adhesiveness after 1 week at room temperature | | |
|---|---|---|---|---|---|---|---|
| | | Tray made of resin | Tray made of MC | Tray made of metal | Tray made of resin | Tray made of MC | Tray made of metal |
| Comparative Example 1 | 18.1 | S | S | S | Gelled | Gelled | Gelled |
| Comparative Example 2 | 18.1 | S | S | S | Gelled | Gelled | Gelled |
| Comparative Example 3 | 18.2 | S | S | S | Gelled | Gelled | Gelled |
| Comparative Example 4 | 18.6 | S | S | S | Gelled | Gelled | Gelled |

In all of the Comparative Examples, the adhesives immediately after preparation exhibited sufficient adhesiveness for the adhesion between all the trays and the impression material. However, when the adhesives were left to stand for one week at 25° C., gelation of the adhesives was observed.

When a comparison was made between the results for Examples 1 to 3 related to the kit for adhesion of a pretreatment agent and an adhesive, which had compositions corresponding to Comparative Examples 2 to 4, and the results for Comparative Examples 2 to 4, Comparative Examples 2 to 4 exhibited slightly poor initial adhesiveness (adhesiveness immediately after preparation).

Comparative Example 5

As shown in Table 6, an adhesion test between various trays and the impression material was carried out by using only the adhesive (C) used in the Examples, without using the pretreatment agent of the present invention. The results are presented in Table 6. In the case of the tray made of a resin, the adhesive strength between the tray and the impression material decreased to a large extent. Since the pretreatment agent that confers a physical interlocking force between the tray and the impression material by swelling and dissolving the surface of the tray, and attaching a fine powder to the tray surface, was not used, the adhesive force decreased.

Comparative Example 6

An adhesion test was carried out on various trays, by using the pretreatment agent (a) of the present invention and the adhesive (C) of the present invention as indicated in Table 6. However, the treatment method was carried out in an order reverse to the treatment method of the present invention. That is, first, the adhesive (C) was applied on the tray, and thereafter, the pretreatment agent (a) was applied on the tray. The results are presented in Table 6. As is obvious from Table 6, since the surface on which the adhesive was applied was disarranged by the pretreatment agent that was applied later, the initial adhesive force to the various trays was decreased to a large extent.

TABLE 6

| | Pretreatment agent | | Adhesive No. | Remarks | Initial adhesiveness | | |
|---|---|---|---|---|---|---|---|
| | No. | Solubility parameter | | | Tray made of resin | Tray made of MC | Tray made of metal |
| Comparative Example 5 | Unused | — | C | Pretreatment agent was not used | VW | VW | VS |
| Comparative Example 6 | a | 18.1 | C | Pretreatment agent and adhesive were used in a reverse order. | VW | VW | VW |

Comparative Examples 7 to 11

Adhesion tests were carried out in the same manner as in Example 1, except that the pretreatment agents and adhesives having the compositions indicated in Table 7 and Table 8 were used. The results are presented in Table 9.

TABLE 7

| | Pretreatment agent composition/parts by mass | | | |
|---|---|---|---|---|
| | Organic solvent | | Inorganic particles | |
| | Ethyl acetate | Ethanol | F2 | F5 |
| a' | 100 | | | 5 |
| b' | 100 | | 0.05 | |
| c' | 100 | | 40 | |

TABLE 8

| | Adhesive composition/parts by mass | | | | |
|---|---|---|---|---|---|
| | Polyamine compound | Organic peroxide | Alcohol-based solvent | Other solvent | |
| | PA3 | BPO | Et—OH | Heptane | Acetonitrile |
| A' | 20 | 5 | | 75 | |
| B' | 20 | 5 | | | 75 |

TABLE 9

| | Pretreatment agent | | Adhesive No. | Initial adhesiveness | | | Adhesiveness after 1 week at room temperature | | |
|---|---|---|---|---|---|---|---|---|---|
| | No. | Solubility parameter | | Tray made of resin | Tray made of MC | Tray made of metal | Tray made of resin | Tray made of MC | Tray made of metal |
| Comparative Example 7 | a' | 18.6 | D | W | W | S | W | W | S |
| Comparative Example 8 | b' | 18.6 | D | VW | VW | S | VW | VW | S |
| Comparative Example 9 | c' | 18.6 | D | VW | VW | VW | VW | VW | VW |
| Comparative Example 10 | c | 18.6 | A' | VS | VS | VS | Adhesive gelled | Adhesive gelled | Adhesive gelled |
| Comparative Example 11 | c | 18.6 | B' | VS | VS | VS | Adhesive gelled | Adhesive gelled | Adhesive gelled |

Comparative Example 7 is a case of using inorganic particles having a particle size of greater than 10 μm in the pretreatment agent. In this case, the adhesion of the inorganic particles to the tray surface was insufficient, and therefore, the adhesiveness of the impression material to the tray made of a resin was decreased.

Comparative Example 8 and Comparative Example 9 are cases in which the amounts of incorporation of the inorganic particles used in the pretreatment agent did not satisfy the conditions of the present invention. In both cases, the effect of incorporating the inorganic particles was not satisfactorily obtained, and the Comparative Examples resulted in a significant decrease in the adhesiveness to the tray made of a resin.

Comparative Examples 10 and 11 are cases in which organic solvents that do not have any alcoholic OH groups were incorporated as the solvent used in the adhesive. In both cases, immediately after the preparation of the adhesives, the impression material adhered to all the trays with high adhesive force. However, when these adhesives were left to stand for one week at 25° C., gelation of the adhesives was observed.

The invention claimed is:

1. A kit for adhesion between an alginate impression material for dental use and an impression tray, the kit comprising:
   (U) a pretreatment agent comprising 100 parts by mass of (I) an organic solvent having a solubility parameter (δ) of 17.0 to 23.0 [(MPa)$^{1/2}$], and 0.1 parts to 30 parts by mass of (II) inorganic particles having an average particle size of 10 μm or less; and
   (V1) an adhesive comprising (I) a polyamine compound containing two or more amino groups in one molecule, and (III) a lower alcohol-based solvent.

2. A kit for adhesion between an alginate impression material for dental use and an impression tray, the kit comprising:
   (U) a pretreatment agent comprising 100 parts by mass of (I) an organic solvent having a solubility parameter (δ) of 17.0 to 23.0 [(MPa)$^{1/2}$], and 0.1 parts to 30 parts by mass of (II) inorganic particles having an average particle size of 10 μm or less; and
   (V2) an adhesive obtained by mixing compounds comprising (I) a polyamine compound containing two or more amino groups in one molecule, (II) an organic peroxide, and (III) a lower alcohol-based solvent.

3. The kit for adhesion between an alginate impression material for dental use and an impression tray according to claim 1, wherein the (I) organic solvent in the (U) pretreatment agent is at least one selected from the group consisting of xylene, toluene, and ethyl acetate.

4. The kit for adhesion between an alginate impression material for dental use and an impression tray according to claim 1, wherein the (III) lower alcohol-based solvent in the (V1) adhesive at least one selected from the group consisting of ethanol, isopropyl alcohol, and n-butanol.

5. The kit for adhesion between an alginate impression material for dental use and an impression tray according to claim 1, wherein the (I) polyamine compound containing two or more amino groups in one molecule in the (V1) adhesive is at least one selected from the group consisting of polyallylamine, polyvinylamine, polyethyleneimine, polyornithine, polylysine, and chitosan.

6. The kit for adhesion between an alginate impression material for dental use and an impression tray according to claim 2, wherein the (V2) adhesive contains 1 part to 50 parts by mass of the (I) polyamine compound containing two or more amino groups in one molecule, 0.1 parts to 30 parts by mass of the (II) organic peroxide, and 20 parts to 98.9 parts by mass of the (III) lower alcohol-based solvent.

7. The kit for adhesion between an alginate impression material for dental use and an impression tray according to claim 2, wherein the (I) organic solvent in the (U) pretreatment agent is at least one selected from the group consisting of xylene, toluene, and ethyl acetate.

8. The kit for adhesion between an alginate impression material for dental use and an impression tray according to claim 2, wherein the (III) lower alcohol-based solvent in the (V2) adhesive is at least one selected from the group consisting of ethanol, isopropyl alcohol, and n-butanol.

9. The kit for adhesion between an alginate impression material for dental use and an impression tray according to claim 2, wherein the (I) polyamine compound containing two or more amino groups in one molecule in the (V2) adhesive is at least one selected from the group consisting of polyallylamine, polyvinylamine, polyethyleneimine, polyornithine, polylysine, and chitosan.

\* \* \* \* \*